United States Patent
Wang

(10) Patent No.: US 7,801,344 B2
(45) Date of Patent: Sep. 21, 2010

(54) EDGE BOUNDARY DEFINITION FOR RADIOGRAPHIC DETECTOR

(75) Inventor: Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 919 days.

(21) Appl. No.: 11/565,780

(22) Filed: Dec. 1, 2006

(65) Prior Publication Data

US 2008/0130976 A1 Jun. 5, 2008

(51) Int. Cl.
*G06K 9/00* (2006.01)
*G06K 9/28* (2006.01)

(52) U.S. Cl. .................. 382/128; 382/132; 382/173; 382/190; 250/584

(58) Field of Classification Search ............. 382/128, 382/132, 173, 190, 199; 250/584
See application file for complete search history.

(56) References Cited

U.S. PATENT DOCUMENTS

| | | | |
|---|---|---|---|
| 4,829,181 A | 5/1989 | Shimura | |
| 5,606,587 A | 2/1997 | Barski et al. | |
| 6,775,399 B1 * | 8/2004 | Jiang | 382/128 |
| 7,003,145 B2 * | 2/2006 | Polkus et al. | 382/132 |
| 7,499,575 B2 * | 3/2009 | Bohm et al. | 382/128 |
| 7,508,970 B2 * | 3/2009 | Jabri et al. | 382/132 |
| 2001/0046312 A1 | 11/2001 | Murakami | |
| 2004/0234133 A1 | 11/2004 | Bohm et al. | |
| 2005/0018893 A1 | 1/2005 | Wang et al. | |

FOREIGN PATENT DOCUMENTS

EP 1 521 209 A2 4/2005

* cited by examiner

*Primary Examiner*—Vikkram Bali
*Assistant Examiner*—Nancy Bitar

(57) ABSTRACT

A method for defining edge boundaries of an image formed on a flat-panel radiographic detector. The method includes obtaining digital image pixel values from the radiographic detector; obtaining dimensional information about a collimator in the radiographic signal path; analyzing the image to detect one or more collimator blade edges; and processing the digital image pixel values at least once to detect remaining collimator blade edges. The method accumulates image pixel values along each of a plurality of lines in a first direction parallel to a first vector that extends across the image, to obtain a first profile value for each line in said first direction, thereby forming an ordered set of first profile values. The method then identifies first and second threshold values in the set of first profile values, wherein the paired first and second threshold values indicate an edge boundary corresponding to a collimator blade projection along the first direction.

6 Claims, 11 Drawing Sheets

EDGE BOUNDARY DEFINITION FOR RADIOGRAPHIC DETECTOR

REFERENCE TO RELATED APPLICATIONS

Reference is made to co-pending U.S. Patent Application Publication No. 2005/0018893 Ser. No. 10/625,919 entitled "Method of Segmenting a Radiographic Image into Diagnostically Relevant and Diagnostically Irrelevant Regions" by Wang et al., filed Jul. 24, 2003 and incorporated herein in its entirety by reference.

FIELD OF THE INVENTION

This invention generally relates to radiography imaging systems using solid-state X-ray detectors, and more particularly relates to defining a region of interest from the image data for improved system processing and image quality.

BACKGROUND OF THE INVENTION

Flat-panel direct digital radiographic (DR) systems and storage phosphor-based computed radiographic (CR) systems provide solid-state imaging systems that are advantaged for many types of X-ray diagnostic imaging. The digital image data that can be directly obtained from these systems can be transmitted, manipulated, displayed or printed, and stored as digital data.

In DR and CR systems, radiation is directed through the subject and impinges upon a detector which is used to form the digital image data, based on the intensity of radiation received at each of a number of pixel locations on the detector. The radiation is modulated by tissue structures of the patient, so that the image data obtained from the detector provides an image of internal tissue structures similar to that obtained from conventional film-based x-ray media.

In different types of x-ray imaging apparatus, the radiation source and radiation detector can be positioned at different angles, suited to the requirements of the type of image that is being obtained. Various angular relationships between source and detector have been found to be particularly advantageous for imaging specific portions of the body and can offer the added benefit of reducing the amount of radiation to which a patient must be exposed.

For X-ray imaging, a collimator, positioned near the X-ray source, provides an aperture of variable size for narrowing the radiation beam, thereby reducing the size of the radiation field to the area being imaged. In a particular embodiment, the collimator has movable horizontal and vertical lead blades, disposed on the sides of the X-ray source, and forms an opening that corresponds to the size of the desired anatomical area and the X-ray sensor.

Generally in digital imaging systems, the larger the image obtained, the greater the amount of image processing required. Factors that impact image processing throughput can include overall image dimensions and pixel spatial and dynamic range resolution. Thus, it is advantageous to electronically identify the region of interest within the image, reducing the size of the imageable area to include substantially only that portion of the anatomy that is of interest (i.e., a region of interest; ROI). A defined region of interest of the image can be more quickly processed and reduces the likelihood of interference from background glare that can be distracting and degrade image appearance when displayed.

In some applications, particularly where the optical centerline of the radiation source is substantially perpendicular to the planar surface of the detector, image cropping can be easily accomplished. This is because values such as collimator opening dimensions, Source-to-Image Distance (SID), and collimator position in the radiation path can be readily determined, allowing for straightforward computation.

However, there are various imaging applications where asymmetrical imaging is required, due to oblique incidence angles of radiation from the radiation source, tilted with respect to the detector surface. For this type of imaging, the issue of ROI definition becomes more complex.

One approach requires the use of sensors, as proposed in U.S. Pat. No. 7,003,145 (Polkus) entitled "Image Cropping for Asymmetrical Imaging". The rotational orientation angles of the radiation source and its collimator is detected using some type of position sensors. A calculation process then employs these angular values in order to compute appropriate image cropping coordinates.

While approaches such as described in Polkus may provide a solution for image cropping with solid-state radiation detectors, there are drawbacks. For example, this type of approach requires the integration of multiple position-sensing components as part of the overall imaging system. The need for tilt sensors and numerous sensors for reporting the position or orientation of imaging components adds complexity and cost to the equipment, adds concerns regarding calibration, is subject to noise and error, and can potentially compromise the robustness of imaging system design. With a design such as that described in Polkus, improper operation of a single sensing component can make it unlikely to automatically identify the area of interest.

Thus, there is a need for an improved, automated image definition method for use with a flat-panel radiographic apparatus, where the region of interest can be readily determined, particularly without requiring the expense and complexity of angular position sensors.

SUMMARY OF THE INVENTION

It is an object of the present invention to provide a method for defining edge boundaries of an image formed on a flat-panel radiographic detector, comprising: a) obtaining digital image pixel values from the radiographic detector; b) obtaining dimensional information about a collimator in the radiographic signal path; c) analyzing the image to detect one or more collimator blade edges; and d) processing the digital image pixel values one or more times to detect remaining collimator blade edges in a procedure comprising: (i) accumulating image pixel values along each of a plurality of lines in a first direction parallel to a first vector that extends across the image, to obtain a first profile value for each line in said first direction, thereby forming an ordered set of first profile values; (ii) identifying first and second threshold values in the set of first profile values, wherein the paired first and second threshold values indicate an edge boundary corresponding to a collimator blade projection along the first direction.

The present invention employs image processing rather than positional instrumentation feedback for determining a suitable image boundary.

The present invention addresses image ROI definition. This method promotes decreased image processing time and reduced image flare, allowing automated image bounding with minimal or no need for operator intervention.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1:
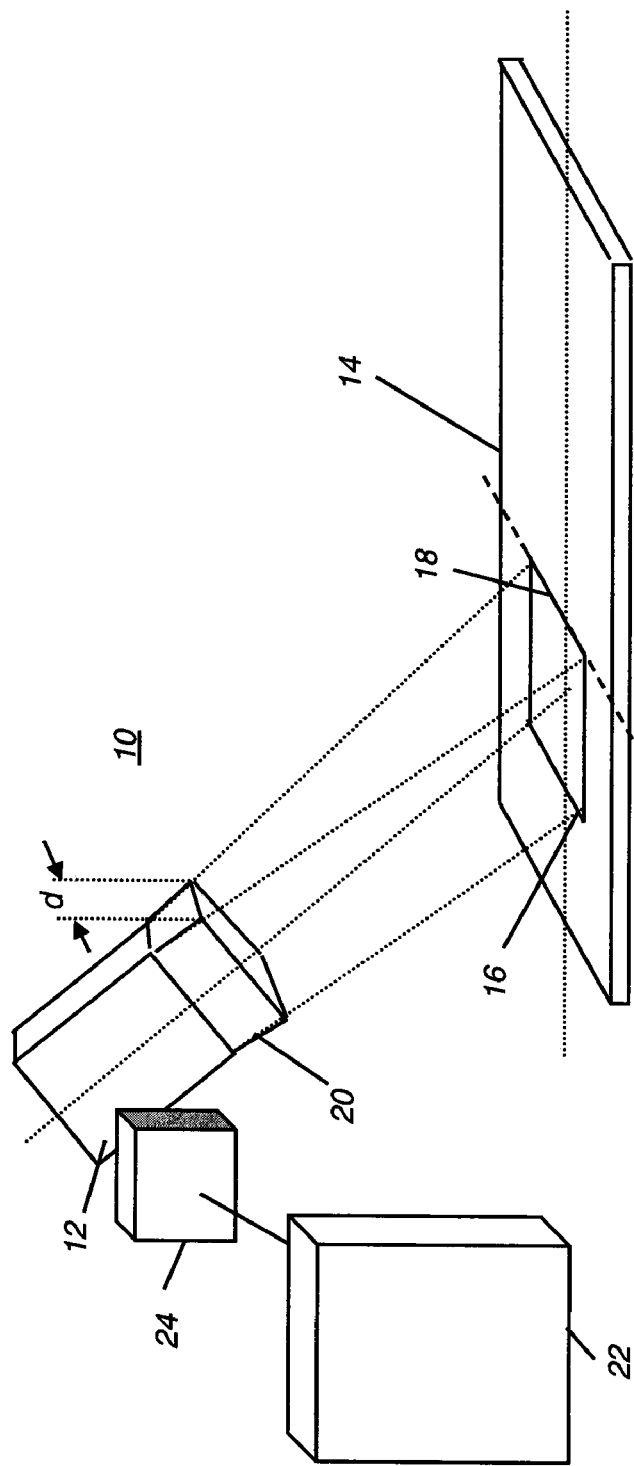
FIG. 1 is a perspective view showing a prior art solid-state flat-panel detector and a radiation source with a collimator.

FIG. 1 generally shows core components of a radiographic imaging apparatus 10 as is well known in the diagnostic imaging arts. Radiographic imaging apparatus 10 has a radiation source 12 that directs radiation through a patient or other object/subject (not shown in FIG. 1) onto a solid-state, flat panel image detector 14. Unlike film cassettes traditionally used for diagnostic X-ray imaging, detector 14 provides electronic image data. The surface of detector 14 converts the radiation energy to light photons, then sensed the intensity of light photons at each of an array of pixel locations. Each pixel is assigned a data value that is related to the intensity of light detected at that location. Detector 14 may be a direct radiography (DR) panel or a computed radiography (CR) panel.

In some systems, radiation source 14 directs its radiation at a normal to the surface of detector 14. However, as is shown in FIG. 1, radiation source 14 may direct its radiation at an angle that is oblique to the surface of detector 14. This type of oblique angle may be of benefit for obtaining various types of images for which perpendicular radiation encounters obstruction or is otherwise less useful. A collimator 20 provides a variably sized aperture, shown with one dimension d, that restricts the radiation field so that only a small image area 16 receives the direct radiation. This arrangement helps to limit the overall amount of radiation received by the patient and to constrain the radiation area to the minimum necessary for obtaining a useful diagnostic image.

One or more collimator edges 18 define image area 16. As shown from the example of FIG. 1, the actual area that is defined as image area 18 depends on a number of factors, including the distance between radiation source 12 and image detector 14, typically expressed as the Source-to-Image Distance (SID). Other factors include the angle of inclination of radiation source 12, usually expressed with respect to a normal to the surface of detector 14 and the aperture opening, as shown by distance d and defined by the variably positioned blades of collimator 20. A collimator sensor 24 provides information on the area of the aperture through which radiation is permitted. Collimator sensor 24 communicates its sensed values with a Control Logic Processor (CPU) 22, such as a computer workstation or dedicated microprocessor, for example. These various distance and angular values determine the size of image area 16, the usable area that contains the image portions that are of interest.

Region of Interest (ROI) definition for the image obtained on detector 14 is useful in a number of ways. Applying a black surround to the image helps both to reduce display flare and minimize processing time, as noted earlier. The method of the present invention provides automated ROI definition based on a small number of hints and assumptions about image collimation in imaging apparatus 10. First, with conventional collimator 20 arrangements, it can be assumed that image area 16 is quadrilateral, or at least polygonal in shape, and does not exceed the usable area of detector 14. Sensor 24 provides a signal that is indicative of the size of the opening of collimator 20.

Figure 2:
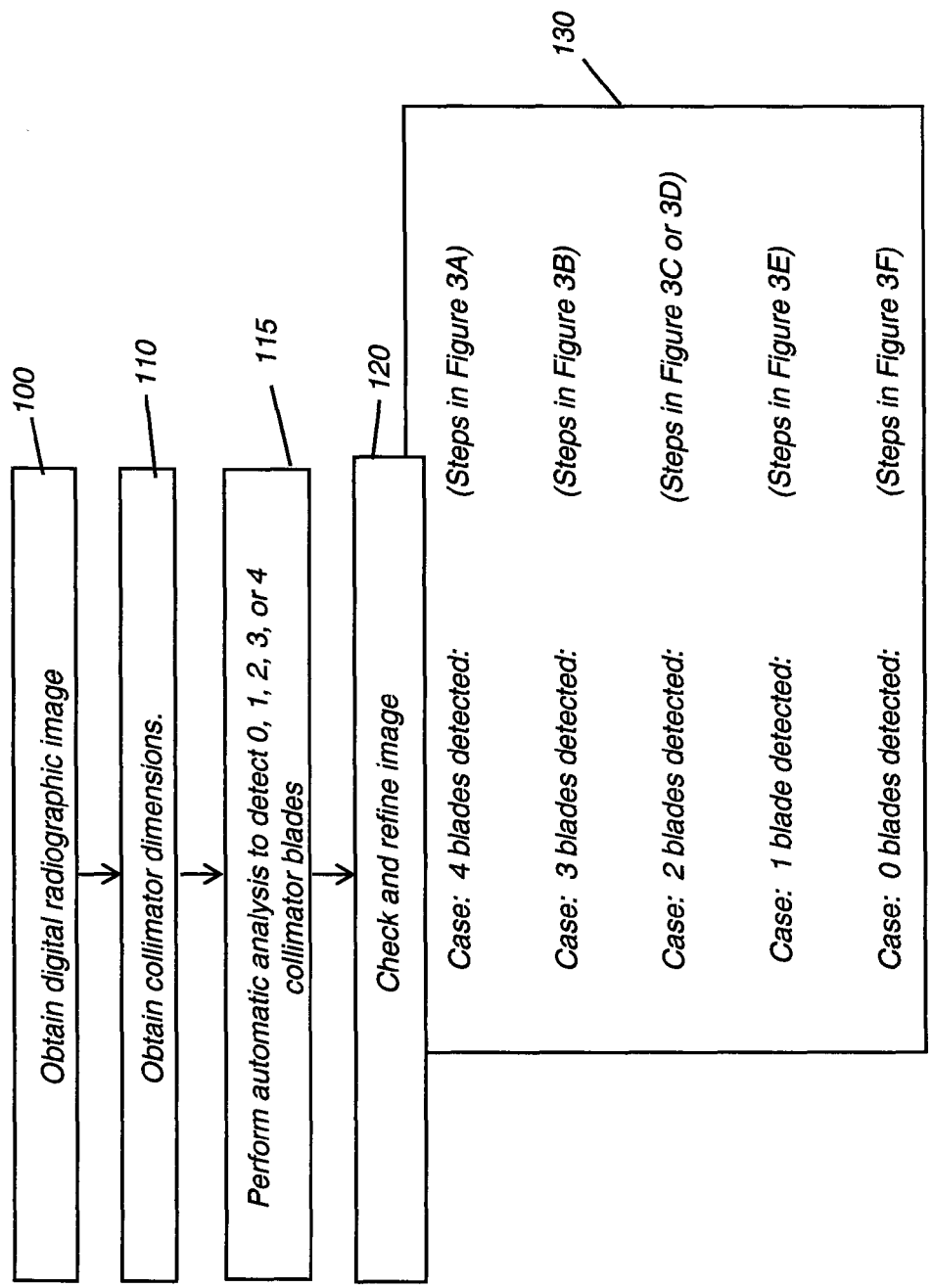
FIG. 2 is a logic flow diagram for the process of the present invention.

The logic flow diagram of FIG. 2 shows steps used for providing ROI definition and black surround according to an embodiment of the present invention.

In an image obtain step 100, the digital radiographic image data is initially read in preparation for image bounding steps that identify edge boundaries corresponding to collimator blade edges. In a collimator dimensions step 110, a signal from sensor 24 is used to compute approximate dimensions of image area 16. As noted above, sensor 24 reports on the overall dimensions of the aperture of collimator 20. Angular information on the rotational position of radiation source 12 may optionally be provided. Information from collimator dimensions step 110 can then be used to provide at least a "hint" as to the approximate size range of image area 16. As is shown in subsequent detailed description, this dimensional hint can then be used as a verification test to support and validate computed data for the position of a well-defined image from imaging detector 14.

Continuing with the method in FIG. 2, an analysis step 115 is executed to detect edge boundaries corresponding to edges of collimator blades from image detector 14. Analysis step 115 determines whether 0, 1, 2, 3, or all 4 collimator blade edges can be identified. This can be determined using procedures such as described in U.S. Patent Application Publication No. 2005/0018893 entitled "Method of Segmenting a Radiographic Image into Diagnostically Relevant and Diagnostically Irrelevant Regions" by Wang et al. Generally, this method extracts the anatomy region of the image by detecting background content from the image histogram, then determining foreground content by a process that uses region growing and related techniques. Other methods can be used for detecting the likely edges of collimator blades in the image, such as methods described in commonly assigned U.S. Pat. No. 5,606,587 entitled "Determination of direct x-ray exposure regions in digital medical imaging" to Barski et al., for example.

A check and refine step 120 is executed, in which the edge(s) of one or more collimator blades may be identified using a capable image segmentation sequence. At worst-case, zero collimator blades are detected within the sensed image data. Check and refine step 120 can be executed in a number of ways. As one example embodiment, the segmentation logic used in commonly assigned U.S. Patent Application Publication No. 2005/0018893 to Wang et al. is applied, hereby incorporated by reference.

These results of check and refine step 120 then determine how the method of the present invention handles detection of the outline of image area 16 for automatic image bounding. A processing step 130, as shown in FIG. 2, provides the procedures for implementing the check and refine process for image data, based on whether 4, 3, 2, 1, or 0 blades of collimator 20 can be detected in the image that is obtained.

Figure 3A:
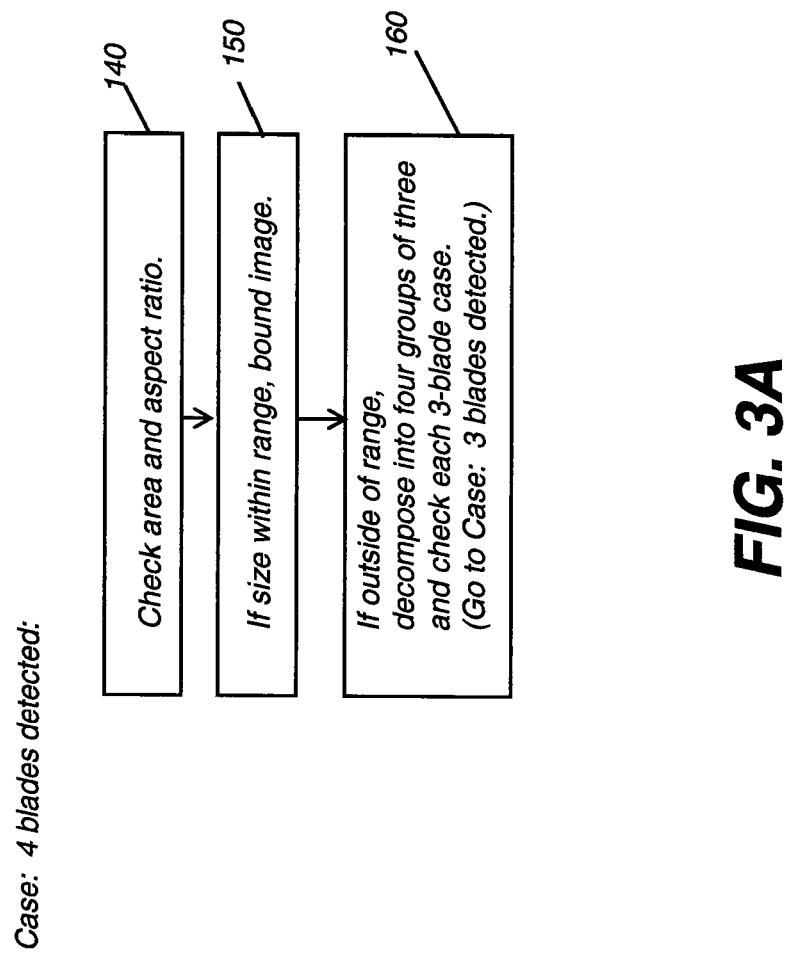
FIG. 3A is a logic flow diagram showing procedures for determining the bounding area in one case, where 4 collimator blades are detected.

FIG. 3A is a logic flow diagram showing procedures for determining the image ROI area in one case, where 4 edge boundaries for collimator blades are detected. An area check step 140 is executed as a part of the check and refine process in this and subsequent processing sequences. Step 140 simply calculates the approximate predicted size for image area 16, as a type of "hint". If subsequent processing yields a value of image area 16 that is grossly larger or smaller than that computed in step 140, an error can be flagged, so that an override or some other error handling routine can be applied for a particular image. In the case of FIG. 3A, since all four blades of collimator 20 appear to have been identified on the image from detector 14, a verification step 150 can be carried out. Verification step 150 checks its computed size for image area 16 against the hint value generated in step 140. If the computed size is reasonably within range of the hint value, an electronic image bounding can be executed, along the detected lines. However, if the computed hint and apparent sensed values differ excessively, a sequence of multiple checks for 3-sided or 3-blade cases can be attempted. A retry step 160 can be performed. Consistent results obtained by considering the 3-blade case of FIG. 3B four times, each time with a different arrangement of 3 sides, can be used to help resolve ambiguity in determining the size and location of image area 16.

Figure 3B:
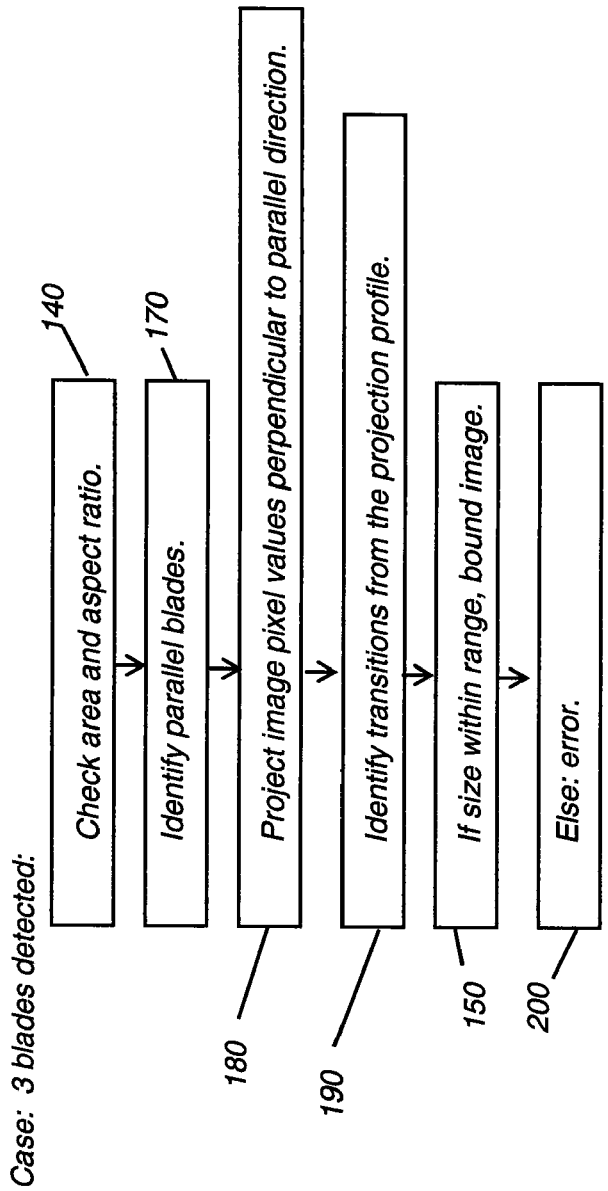
FIG. 3B is a logic flow diagram showing procedures for determining the bounding area in one case, where 3 collimator blades are detected.

FIG. 3B is a logic flow diagram showing procedures for determining the bounding area in the case where 3 edge boundaries for collimator blades are detected. In such a case, since image area 16 is a quadrilateral, two of the 3 collimator blades will be disposed in parallel. A hint value is again generated in step 140. A parallel blades identification step 170 uses straightforward image processing routines to identify the image of the two parallel blades of collimator 20. Once the parallel structures have been identified, an accumulation step 180 can be executed. Briefly, accumulation step 180 profiles values from the image that lie along a direction parallel to a vector and detects a transition in accumulated pixel values that can be used to indicate the border region of an image, by detecting the shadow (image) of a collimator blade, that is, its projected edge boundary, that lies perpendicular to a direction.

Figure 4:
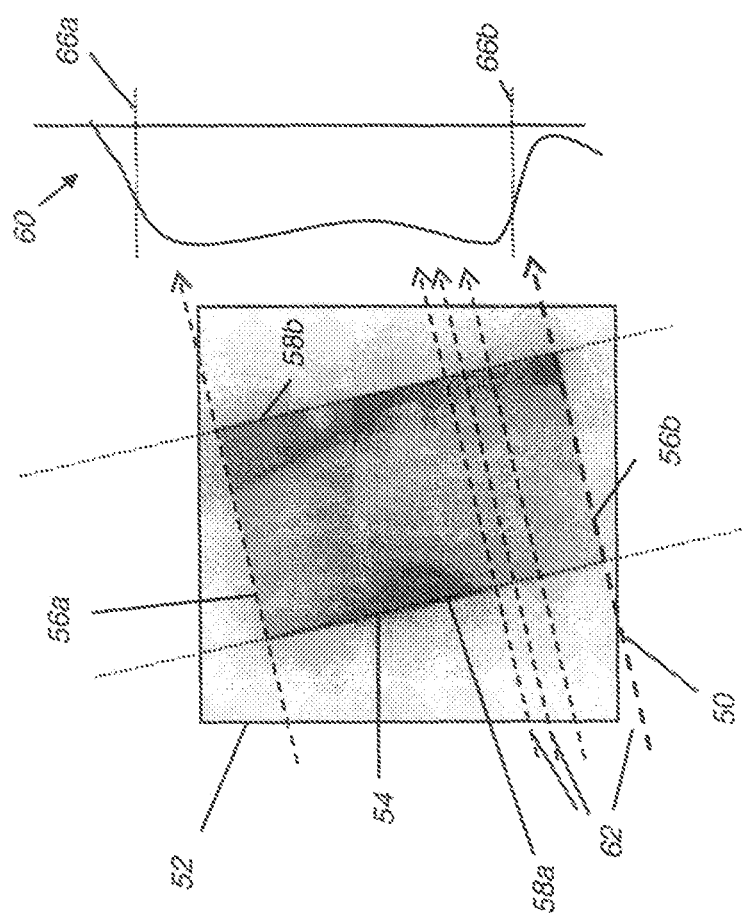
FIG. 4 is a schematic diagram showing one pixel value accumulation scheme for pixels parallel to a vector.
Figure 5:
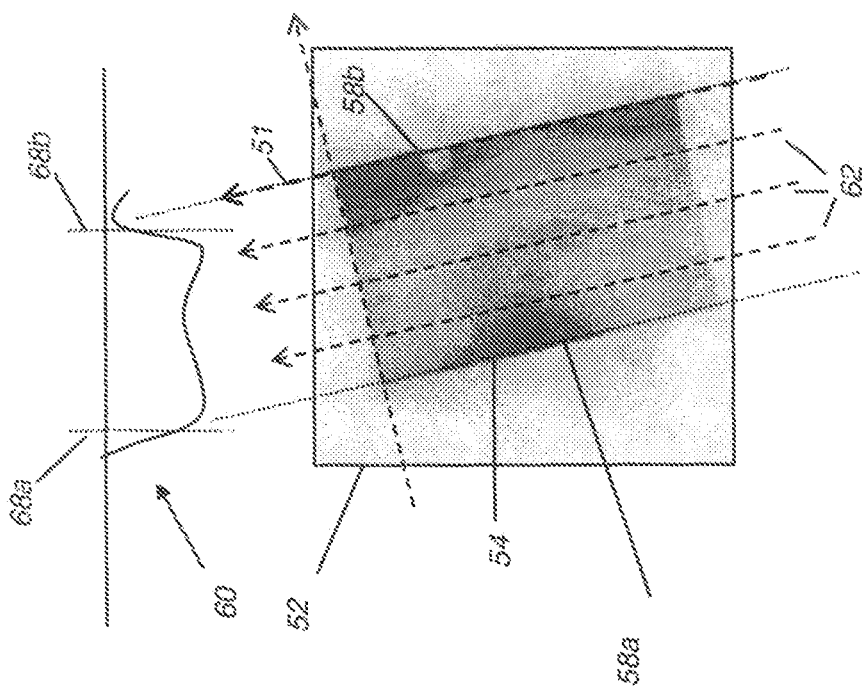
FIG. 5 is a schematic diagram showing one pixel value accumulation scheme for pixels perpendicular to a vector.

The schematic views of FIGS. 4 and 5 show how accumulation step 180 can be executed according to one embodiment. In FIG. 4, a vector 50 is traced in a direction across an image 52 that contains the full set of pixels returned from detector 14. Vector 50 direction is determined based on the resulting edges found from analysis step 115. The image bounding method of the present invention identifies the boundaries used for obtaining a bounded image 54 from image 52 by detecting the two sets of parallel blade images 56a and 56b and 58a, 58b. These two sets are substantially orthogonal with respect to each other.

The accumulation process is carried out along lines 62 that are parallel to vector 51 and can be performed in a number of ways. In one embodiment, accumulation step 180 uses a straightforward pixel averaging algorithm that adds the intensity values for all pixels along line 62 and averages the accumulated sum by the number of pixels on this line 62 to obtain a result. This accumulation method provides a projection profile 60, in which each result value is then plotted against its corresponding line number. As can be observed from projection profile 60 in FIG. 4, it is possible to identify threshold values 66a and 66b that roughly correspond to the edge boundaries defined by blade images 56a and 56b. Using this characteristic, the general position of either or both blade images 56a and 56b can be located. As shown in FIG. 5, this same type of accumulation process can be used in the orthogonal direction for obtaining threshold values 68a and 68b that correspond to parallel blade images 58a and 58b, here based on lines 62 that are parallel to a vector 51. Vector 51 is perpendicular to vector 50.

It can be appreciated that other types of accumulation computation can be used to profile successive lines 62 of image 52 that are parallel to either of two orthogonal vectors 50 (as in FIG. 4) and 51 (as in FIG. 5). Of particular interest for detection of blade image 56a, 56b, 58a, 58a edge boundaries is a transition that can be detected according to accumulated values.

Referring again to FIG. 3B, a threshold detection step 190 is performed to detect blade edges, such as by detecting threshold values 66a, 66b, 68a, and 68b in the illustrative example of FIGS. 4 and 5. Verification step 150 checks the size of the detected image area and, if within the range that corresponds to the hint value obtained from the system collimator hardware, defines the image boundary. An optional error handling step 200 is executed where some problem is detected, alerting the equipment operator or performing some other function for resolving image definition problems.

Figure 3C:
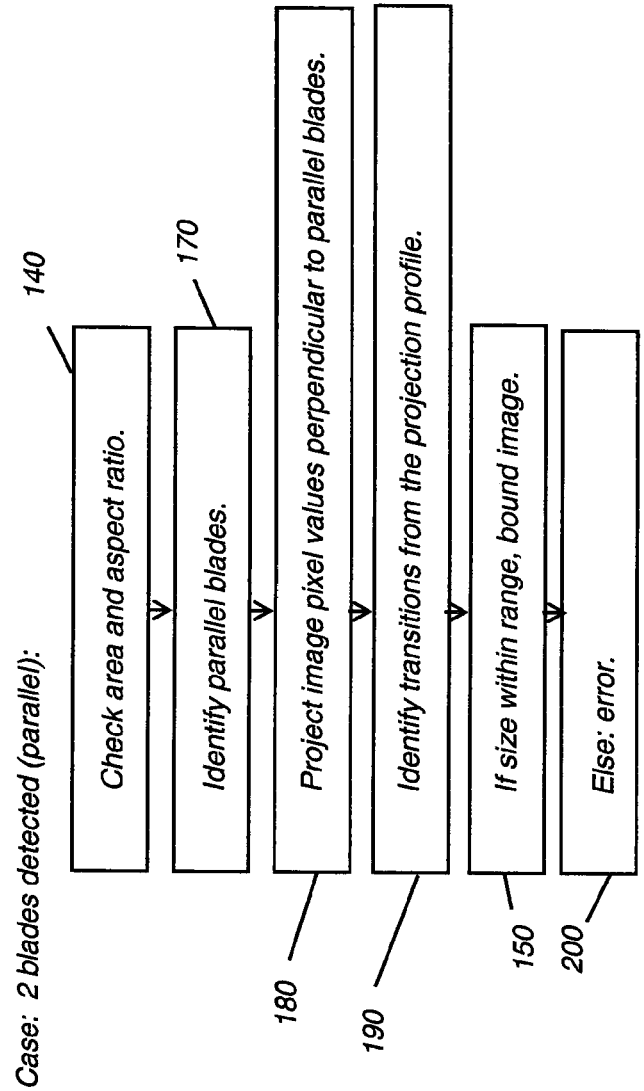
FIGS. 3C and 3D are logic flow diagrams showing procedures for determining the bounding area in cases where 2 collimator blades are detected.
Figure 6:
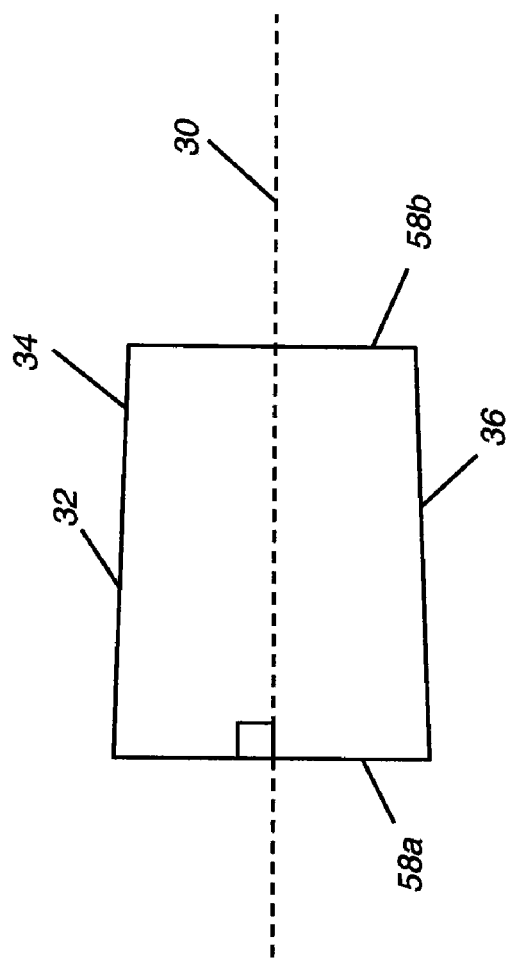
FIG. 6 is a schematic diagram showing use of averaging to obtain an approximate parallel to detected lines.

The logic sequence of FIG. 3C can be applied where only two blade images are detected as edge boundaries and these detected edge boundaries are in parallel. Referring to FIG. 4, for example, this would be the situation if either pair of blade images 58a and 58b or blade images 56a and 56b were detected. As described with reference to FIG. 3B, following computation of a hint based on area and aspect ratio information from the collimator hardware, parallel blades identification step 170 is applied to identify the image of the two parallel blades of collimator 20. Accumulation step 180 is then executed, followed by threshold detection step 190 for detecting the other parallel blade edges. As part of this step, as shown in FIG. 6, where lines for blade image 58a and 58b are detected and in parallel, edges 34 and 36 of an outline 32 may not be parallel due to slight "keystone" effects. In such a case, an averaged line 30, shown by a dashed line in FIG. 6, is used as an approximation for the blade edges represented by edges 34 and 36. Line 30 is substantially parallel to the detected parallel edges, providing some measure of compensation for radiation incidence at an oblique angle. Verification step 150 checks the size of the detected image area and, if within the range that corresponds to the hint value obtained from the system collimator hardware, defines the image boundary. As was described with reference to FIG. 3B, optional error handling step 200 is executed where some problem is detected, alerting the equipment operator or performing some other function for resolving image definition problems.

Figure 3D:
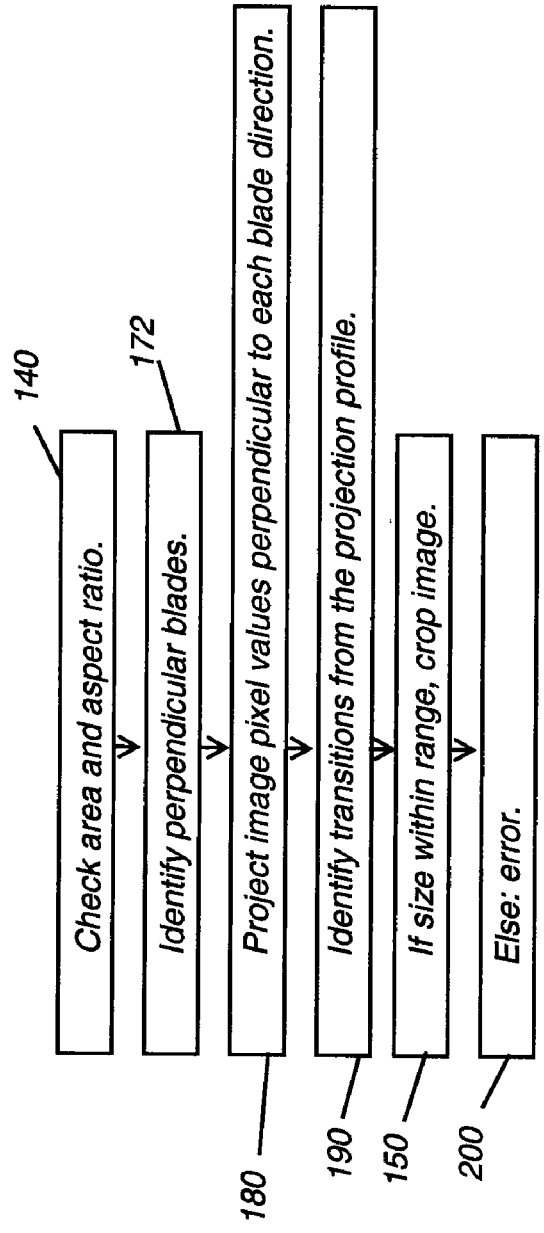

The logic sequence of FIG. 3D applies where only two blade images are detected as edge boundaries and these detected blade images are perpendicular. Referring to FIG. 4, for example, this would be the situation if one element from either pair of blade images 58a or 58b and one element from either pair of blade images 56a or 56b were detected. A perpendicular blades identification step 172 is applied to identify the image of the two perpendicular blades of collimator 20. Accumulation step 180 is again executed, followed by threshold detection step 190 for detecting the other parallel blade edges. Verification step 150 checks the size of the detected image area and, if within the range that corresponds to the hint value obtained from the system collimator hardware, defines the image boundary. As was described with reference to FIG. 3B, optional error handling step 200 is executed where some problem is detected, alerting the equipment operator or performing some other function for resolving image definition problems.

Figure 3E:
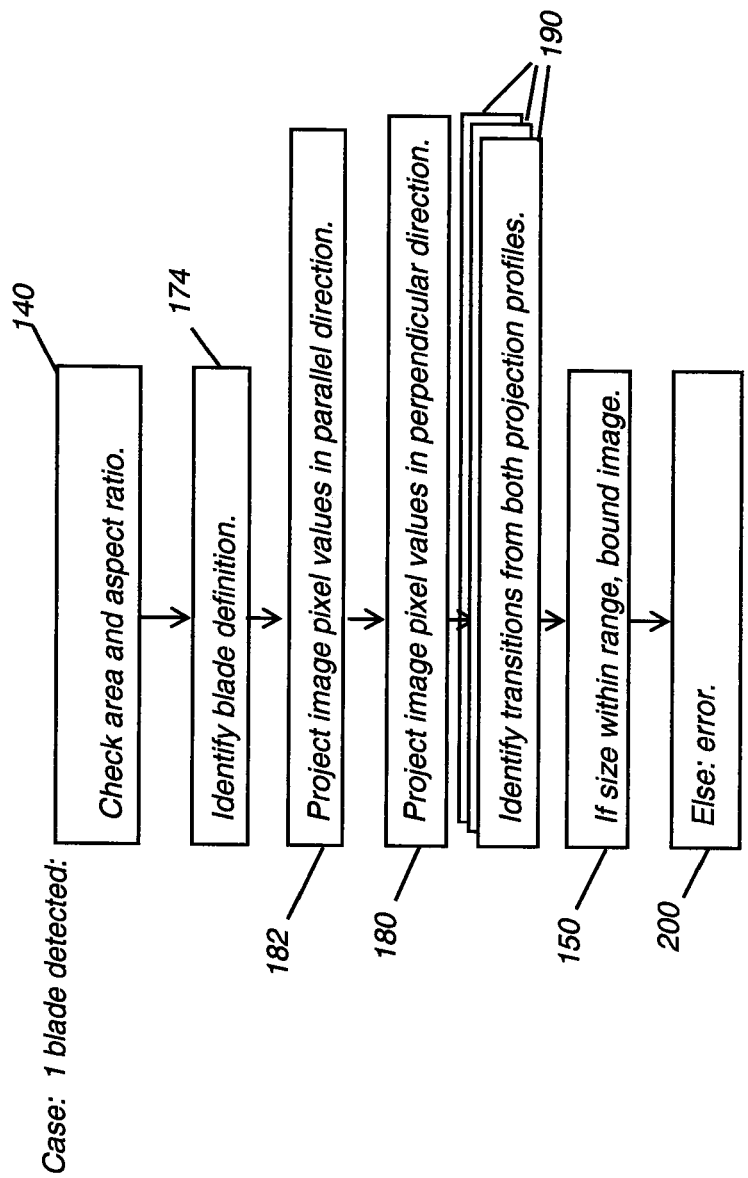
FIG. 3E is a logic flow diagram showing procedures for determining the bounding area in one case, where 1 collimator blade is detected.

The logic sequence of FIG. 3E applies where only one blade image is detected as a single edge boundary. The control logic computes a hint value in step 140. Then, a single blade identification step 174 is carried out to identify the location of the identified blade image 56a, 56b, 58a, or 58b. The blade edge that has been identified is then used as a base reference and lines are projected in the directions parallel to and perpendicular to this edge, in accumulation steps 180 and 182. Threshold detection step 190 is then used multiple times, on both parallel and perpendicular projections, to identify transitions that indicate collimator blade images 56a, 56b, 58a, or 58b. Verification step 150 checks the size of the detected image area and, if within the range that corresponds to the hint value obtained from the system collimator hardware, defines the image boundary. As was described with reference to earlier procedures, optional error handling step 200 is executed where some problem is detected, alerting the equipment operator or performing some other function for resolving image definition problems.

Figure 3F:
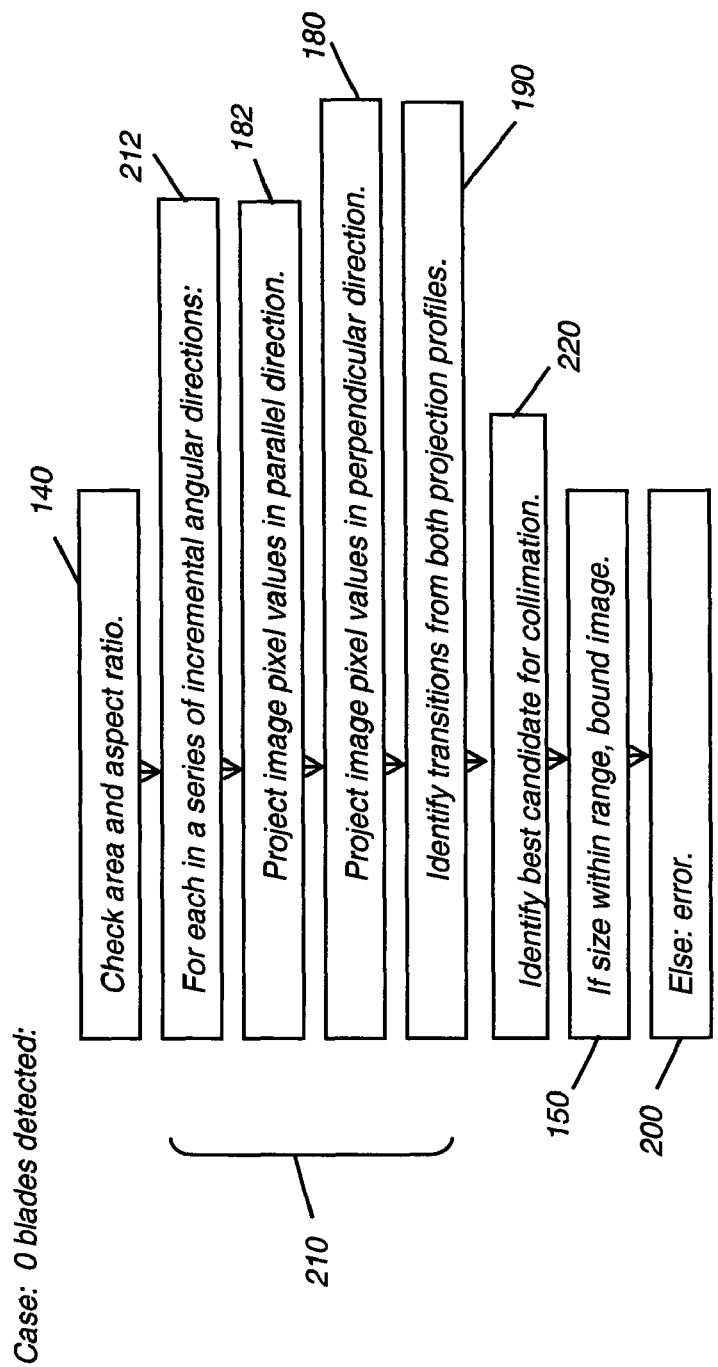
FIG. 3F is a logic flow diagram showing procedures for determining the bounding area in one case, where no collimator blades are detected.

FIG. 3F is a logic flow diagram showing procedures for determining the image ROI area where no collimator blades are initially detected. Under these conditions, a significant amount of pixel projection and computation is used in order to identify the best candidates for collimator blade images 56a, 56b, 58a, or 58b. The control logic initially computes a hint value in step 140. Then, a control loop 210 is executed a number of times, using vectors in different angular directions. A first angular direction is selected in an angle selection step 212. Then, lines are projected in the directions parallel to and perpendicular to this angular direction, in accumulation steps 180 and 182. Threshold detection step 190 is then used in each direction, that is, on both parallel and perpendicular projections, to identify transitions that might indicate collimator blade images 56a, 56b, 58a, or 58b. Results are scored in some manner and information stored about results in the two projection directions. Then, control loop 210 is repeated, with angle selection step 212 choosing another angle, such as by incrementing the previously selected angle by one degree, for example. Accumulation steps 180 and 182 are again repeated, as is threshold detection step 190 for projection in each direction. Scored results are again scored and control loop 210 again repeated until a complete angular sweep has been made through bounded image 54. For example, where one degree increments are added with each iteration of control loop 210, 89 iterations would provide the useful data necessary to locate collimator blade images 56a, 56b, 58a, or 58b. Comparison of scored values would be performed in a candidate identification step 220.

The method of the present invention addresses defining the image ROI and offers the potential benefits of decreased image processing time and reduced image flare, without the need for operator intervention. The present method employs a minimum of feedback information from the imaging apparatus and uses this information for verification. Thus, costly and error-prone orientation sensors need not be installed in the digital radiography system in order to define the image boundary. The method of the present invention uses the image data from the flat-panel digital detector itself to determine image boundaries. The invention can be used with solid-state imaging panels from both direct digital radiographic (DR) systems and storage phosphor-based computed radiographic (CR) systems. Detection of the image area size in verification step 150 can be simply performed using computed Euclidean distances based on pixel dimensions and overall size of the solid-state flat-panel detector. Once the image boundary has been defined, a black surround or other image treatment can be used to suppress unwanted portions of the image and to outline that portion of the obtained image that contains the ROI.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, there are a number of algorithms that could be applied to edge detection problems and could, therefore, be used for identifying the edges of the useful portion of a digital image. Candidate selection and scoring, noted with reference to the process shown in FIG. 3F, could be performed in any of a number of ways familiar to those skilled in the image processing arts.

Thus, what is provided is an apparatus and method for determining the boundaries of image data for improved system processing and image quality in a digital radiography apparatus.

PARTS LIST

10 Imaging apparatus
12 Radiation source
14 Image detector
16 Image area
18 Edge
20 Collimator
22 Control logic processor
24 Sensor
30 Line
32 Outline
34, 36 Edge
50, 51 Vector
52 Image
54 Bounded image
56a, 56b Blade image
58a, 58b Blade image
60 Projection profile
62 Line
66a, 66b Threshold value
68a, 68b Threshold value
100 Image obtain step
110 Collimator dimensions step
115 Analysis step
120 Check and refine step
130 Processing step
140 Area check step
150 Verification step
160 Retry step
170 Parallel blades identification step
172 Perpendicular blades identification step
174 Single blade identification step 180, 182 Accumulation step
190 Threshold detection step
200 Error handling step
210 Control loop
212 Angle selection step
220 Candidate identification step
d Dimension

The invention claimed is:

1. A method for defining edge boundaries of an image formed on a flat-panel radiographic detector, comprising:
   obtaining digital image pixel values from the radiographic detector;
   obtaining dimensional information about a collimator in the radiographic signal path;
   analyzing the image to detect one or more collimator blade edges; and
   processing the digital image pixel values at least once to detect remaining collimator blade edges by:
   (i) accumulating image pixel values along each of a plurality of lines in a first direction parallel to a first vector, determined by the orientation of a detected collimator blade edge, that extends across the image, to obtain a first profile value for each line in said first direction, thereby forming an ordered set of first profile values; and
   (ii) identifying first and second threshold values in the set of first profile values, wherein the paired first and second threshold values indicate an edge boundary corresponding to a collimator blade projection along the first direction.

2. The method of claim 1 wherein processing the digital image pixel values at least once further comprises the steps:
   (iii) accumulating image pixel values along each of a plurality of lines in a second direction perpendicular to the first vector, to obtain a second profile value for each line in said second direction, thereby forming an ordered set of second profile values; and
   (iv) identifying third and fourth threshold values in the set of second profile values, wherein the paired third and fourth threshold values indicate an edge boundary corresponding to a collimator blade projection along the second direction.

3. The method of claim 2 further comprising applying a black surround to that portion of the image that lies outside each detected edge boundary.

4. The method of claim 1 wherein processing the digital image pixel values further comprises:
   obtaining measurement data about the collimator; and
   testing the first edge boundary against a calculated dimensional limit for collimator blade projection according to the measurement data.

5. A method for defining an image formed on a flat-panel radiographic detector, comprising:
   obtaining digital image pixel values from the radiographic detector;
   computing a maximum image size according to collimator opening dimensions and the source-to-image distance;
   analyzing the image to detect one or more collimator blade edges;
   processing the digital image pixel values one or more times by:
   (i) accumulating image pixel values along each of a plurality of lines in a first direction parallel to a first vector, determined by the orientation of a detected collimator blade edge, that extends across the image, to obtain a first profile value for each line in said first direction, thereby forming an ordered set of first profile values;
   (ii) identifying first and second threshold values in the set of first profile values, wherein the paired first and second threshold values indicate an edge boundary corresponding to a collimator blade projection along the first direction;
   (iii) accumulating image pixel values along each of a plurality of lines in a second direction perpendicular to the first vector to obtain a second profile value for each line in said second direction, thereby forming an ordered set of second profile values; and
   (iv) identifying third and fourth threshold values in the set of second profile values, wherein the paired third and fourth threshold values indicate an edge boundary corresponding to a collimator blade projection along the second direction; and
   defining the image boundary according to the edge boundaries obtained.

6. A method for defining an image formed on a flat-panel radiographic detector, comprising:
   obtaining digital image pixel values from the radiographic detector;
   obtaining a signal indicative of at least one dimension of a collimator opening;
   analyzing the image to detect one or more collimator blade edges;
   processing the digital image pixel values one or more times by:
   (i) accumulating image pixel values along each of a plurality of lines in a first direction parallel to a first vector, determined by the orientation of a detected collimator blade edge, that extends across the image, to obtain a first profile value for each line in said first direction, thereby forming an ordered set of first profile values;
   (ii) identifying first and second threshold values in the set of first profile values, wherein the paired first and second threshold values indicate an edge boundary corresponding to a collimator blade projection along the first direction;
   (iii) accumulating image pixel values along each of a plurality of lines in a second direction perpendicular to the first vector to obtain a second profile value for each line in said second direction, thereby forming an ordered set of second profile values; and
   (iv) identifying third and fourth threshold values in the set of second profile values, wherein the paired third and fourth threshold values indicate an edge boundary corresponding to a collimator blade projection along the second direction;
   comparing the at least one dimension of the collimator opening with a computed distance between parallel edge boundaries identified in step (c);
   defining the image boundary according to the edge boundaries obtained; and
   applying a black surround to areas lying outside the defined image boundary.

* * * * *